United States Patent [19]

Schlumberger

[11] Patent Number: 4,495,816

[45] Date of Patent: Jan. 29, 1985

[54] PROCESS AND SYSTEM FOR ANALYZING DISCONTINUITIES IN REASONABLY HOMOGENEOUS MEDIUM

[75] Inventor: Etienne Schlumberger, Paris, France

[73] Assignee: Medical Devices, Inc., San Francisco, Calif.

[21] Appl. No.: 495,265

[22] Filed: May 17, 1983

[30] Foreign Application Priority Data

May 21, 1982 [FR] France .................................. 82 08883

[51] Int. Cl.³ ........................................... G01N 29/04
[52] U.S. Cl. ........................................ 73/600; 73/602; 73/618; 367/30; 364/422; 364/577; 128/660
[58] Field of Search ................ 73/599, 600, 597, 598, 73/602, 618, 620, 625, 626, 628; 364/422, 577; 367/28, 30; 181/104; 128/660; 324/333, 334, 346, 351, 372

[56] References Cited

U.S. PATENT DOCUMENTS

| | | | |
|---|---|---|---|
| 2,388,703 | 11/1945 | Peterson | 367/36 |
| 2,599,688 | 6/1952 | Brant | 324/372 |
| 3,685,051 | 8/1972 | Wells | 73/603 |
| 4,130,112 | 12/1978 | Frazer | 73/633 |
| 4,172,250 | 10/1979 | Guignard | 367/28 |
| 4,313,163 | 1/1982 | Mizutani | 364/577 |
| 4,322,974 | 4/1982 | Abele et al. | 73/602 |
| 4,340,934 | 7/1982 | Segesman | 364/422 |

FOREIGN PATENT DOCUMENTS 1161080 8/1969 United Kingdom .

OTHER PUBLICATIONS

G. H. Glover et al., "Reconstruction of Ultrasound Propagation Speed Distributions in Soft Tissue: Time of Flight Tomography", IEEE Trans. on Sonic and Ultrasonics, vol. SU24, No. 4, pp. 229–234, Jul. 1977.

Primary Examiner—Stephen A. Kreitman
Attorney, Agent, or Firm—Poms, Smith, Lande & Rose

[57] ABSTRACT

According to the process signals adapted to the medium and to the kind of discontinuity to be analyzed are transmitted towards the discontinuity from a number of transmitting points located on at lease one base line, these signals are received at a number of reception points located on at least one base line placed on the opposite side of the discontinuity as far as the transmission paths are concerned; the received signals are then analyzed to obtain the position and shape of the discontinuity. In certain cases the echos and backscatter are also analyzed. At least one of the base lines $F_1$ carrying the transmission points does not intersect with at least one of the other base lines carrying the reception points. This system and method may be used to determine the position and shape of underground discontinuities, to analyze the internal structure of human or animal bodies, or any other inanimate object in any medium.

17 Claims, 13 Drawing Figures

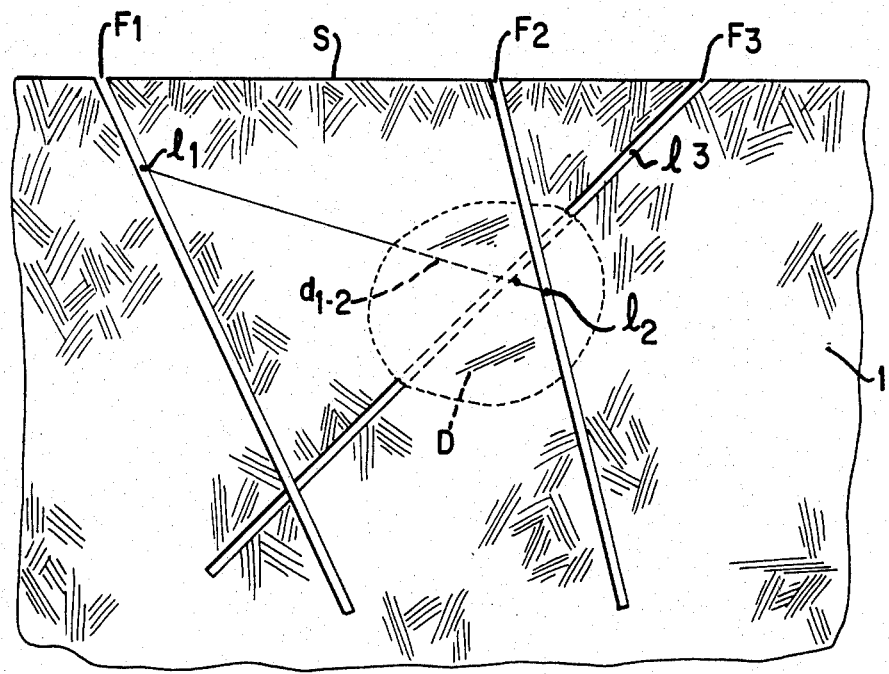
FIG_1
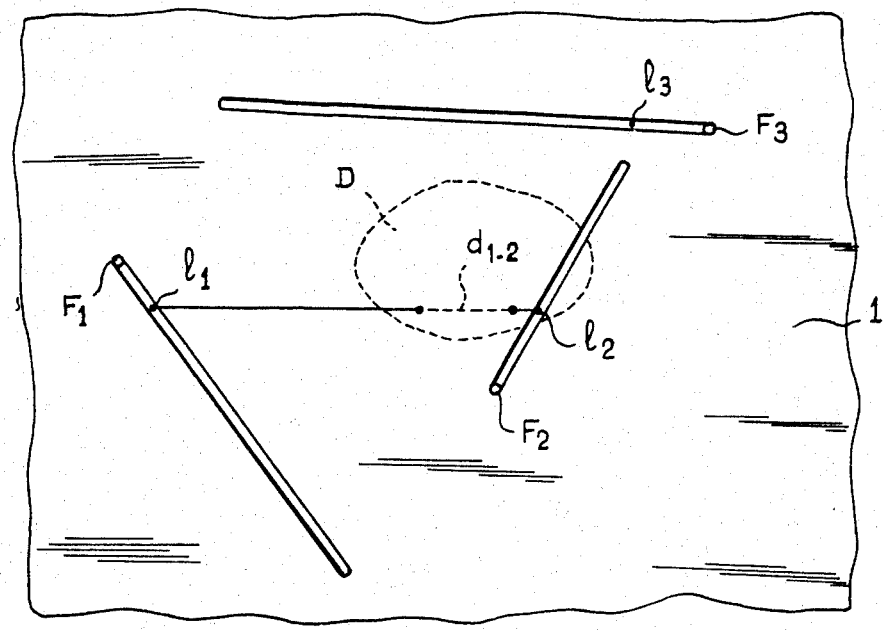
FIG_2

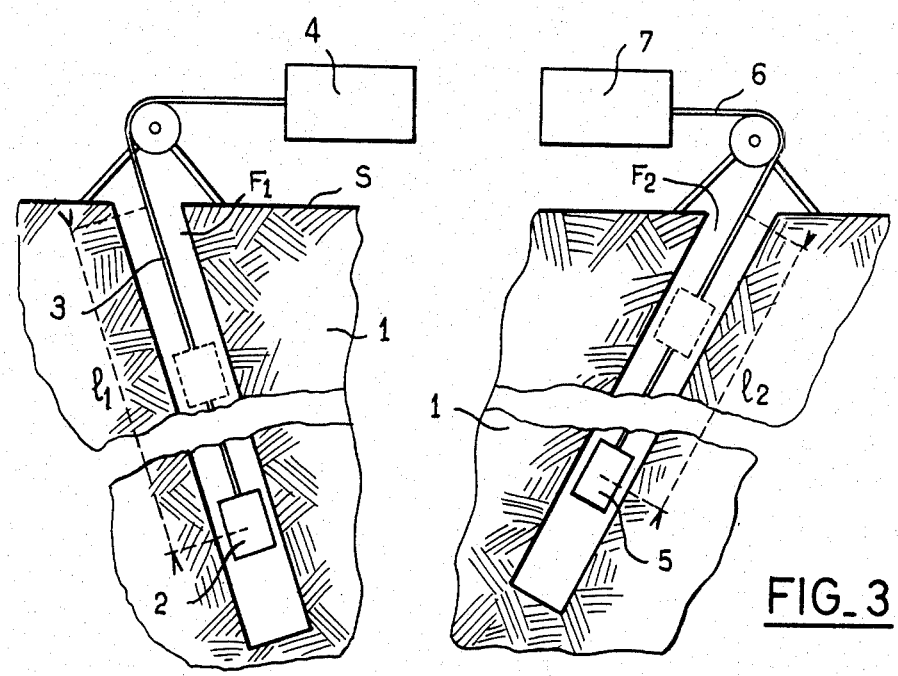
FIG_3
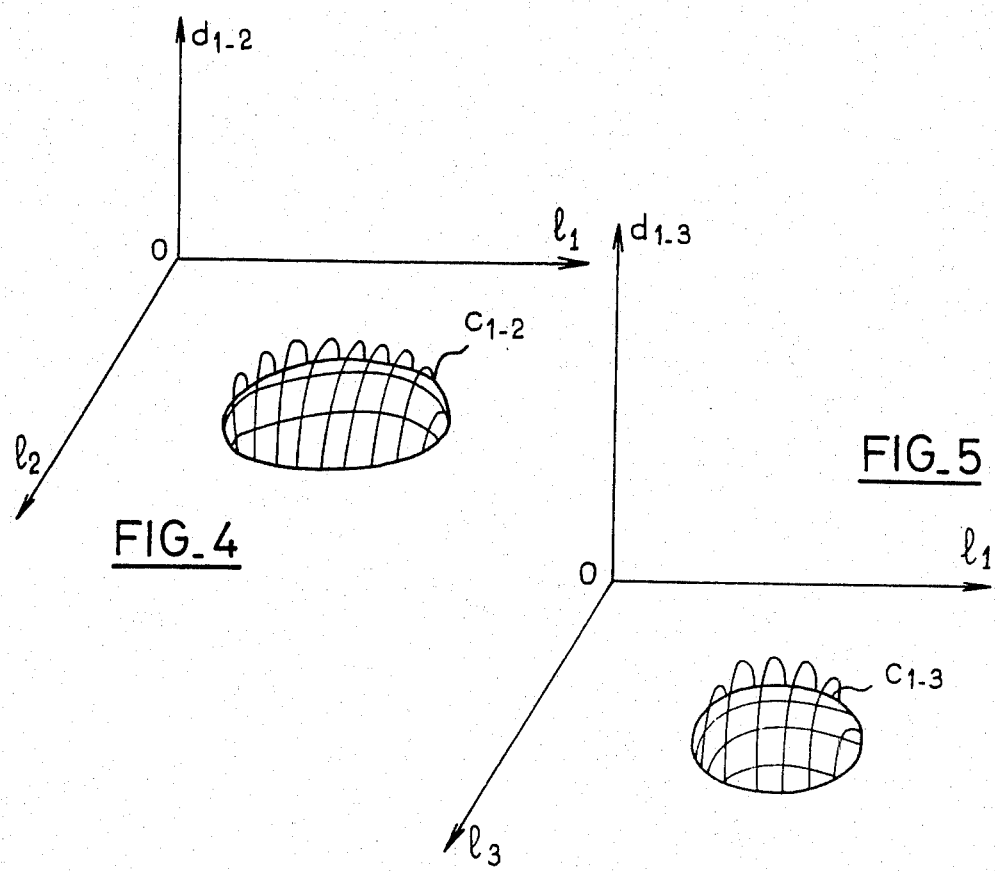
FIG_4
FIG_5

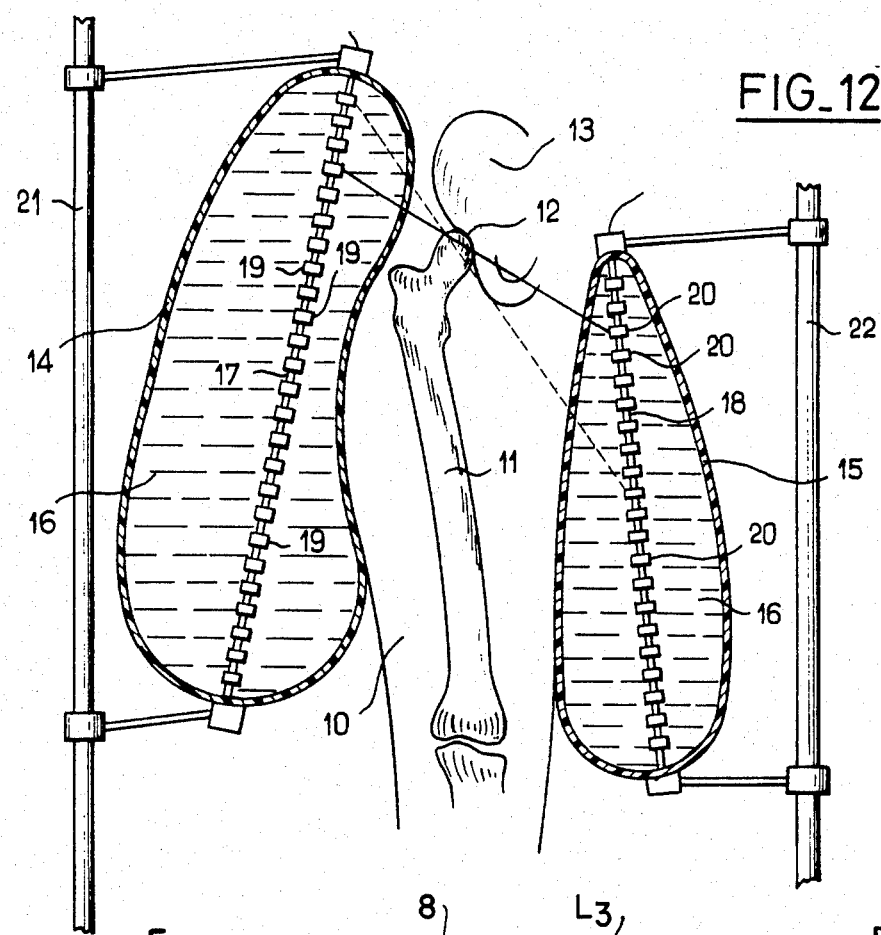
FIG_12
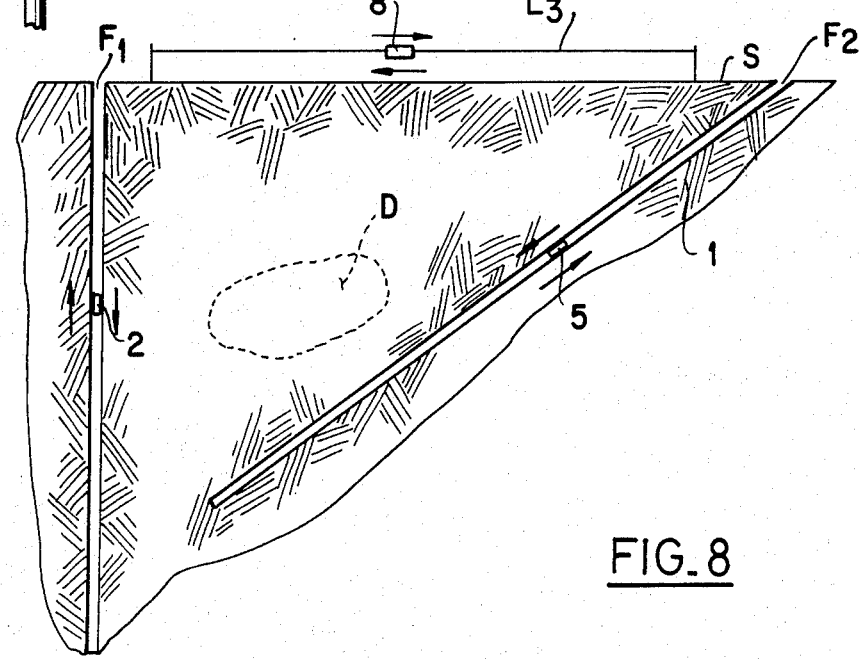
FIG_8

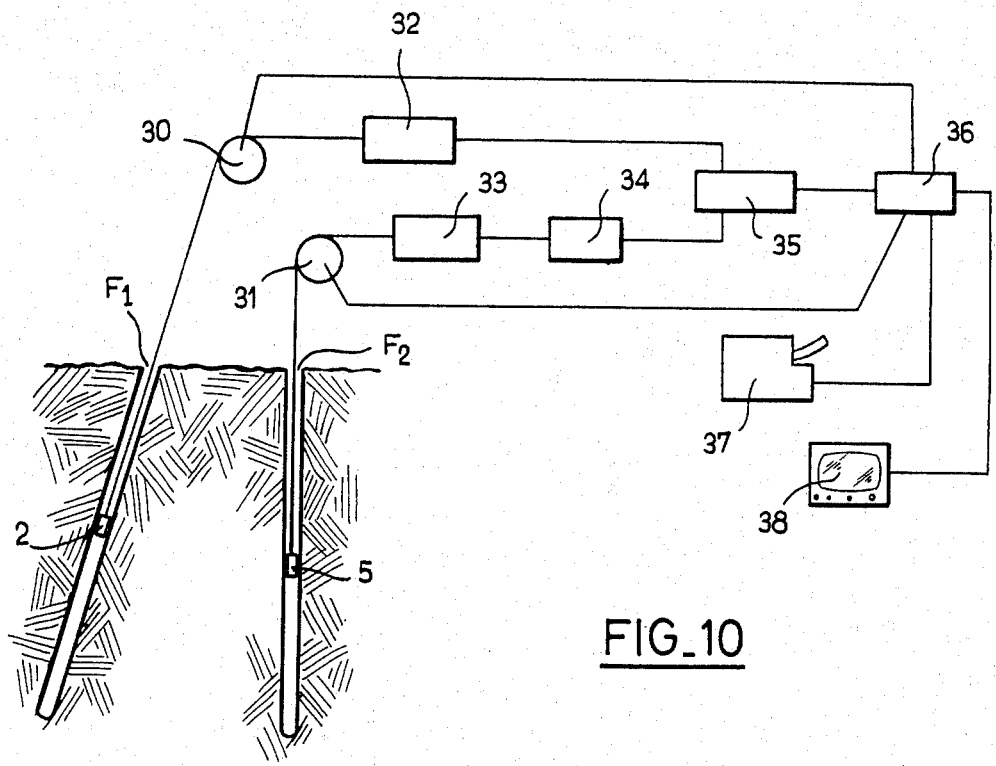
FIG_10
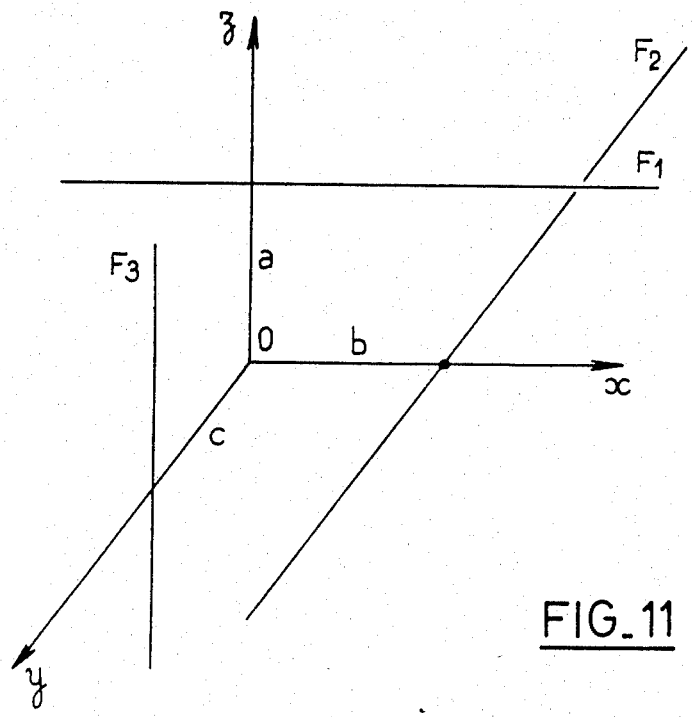
FIG_11

PROCESS AND SYSTEM FOR ANALYZING DISCONTINUITIES IN REASONABLY HOMOGENEOUS MEDIUM

The present invention relates to a process for analyzing discontinuities situated in a reasonably homogeneous medium such as earth or the interior of the human body or that of an animal.

BACKGROUND OF THE INVENTION

In various fields from geology to medicine the search and analysis of deep discontinuities can be of great importance. As an example it can be very desirable in the ground to find the location and shape of discontinuities such as cavities, mineral deposits, accumulations of hetergenous materials, archeological ruins, munitions, etc.

In medicine ultrasonics are used in echography, (sonar-like reflection analysis), and x-rays in radiography and scanners in order to analyse the organs or interal injuries to the human body.

Up to the present, outside of the field of radiography which uses point source transmitters, most other systems involve the analysis of parallel planar sections of the volume; then from successive planar sections, attempts are made to reproduce the entire three dimensional volume.

U.S. Pat. No. 4,161,687 discloses as an example a method to detect small dimension discontinuities such as a cavity located between two verticle boreholes. This discontinuity is analysed within the plane defined between the two verticle boreholes and utilizing high frequency signals transmitted from one borehole to the other.

In order to image precisely the location and the shape in three dimensions of such a discontinuity a great number of boreholes would be necessary to obtain the analysis of enough sections of the discontinuity in all of the planes defined by various pairs of boreholes. The number of boreholes required is a function of the complexity and of the dimensions of the discontinuity and of the required definition. As an example, in a general approach, approximately 10 boreholes might be required. The major drawback of this method is the high cost of numerous boreholes.

In medicine the scanner analyses the human body by a number of parallel sections which give a three dimensional image when combined. In the same manner echography establishes a number of planar sections of the human body which by superposition or combination can give a general image of a possible anomaly inside the human body. The definition of the analysis is a function of the number and proximity of parallel sections which are utilized. The drawback of such a system is the high cost due to the complexity.

The object of the present invention is to avoid the drawbacks of existing methods by using a new process and system to analyse the discontinuities either undergound or in an animal or human body, with the methods and system being much simpler and less costly than those which have been proposed heretofore.

SUMMARY OF THE INVENTION

In the present invention, signals suited to the medium and the discontinuity are transmitted toward the discontinuity from a number of successive points located on a line. These signals are received at a series of locations situated on at least one other line on the other side of the discontinuity; and the analysis of these received signals gives the shape and location of the discontinuity.

According to one aspect of the invention the process is characterized by the fact that at least one of the lines containing the transmitting positions does not intersect one of the lines containing the receiving positions.

The process of the present invention is based on the following principles: If one considers two practically straight lines in space and if one associates all of the points on one line to all of the points on the other line, all the lines joining all these points, two by two, are situated in a plane if the two base lines intersect or are parallel. On the other hand if the two base lines neither intersect nor are parallel, the total of these lines intersecting both base lines covers the entire space. Effectively, any point of space determines a plane with one of the base lines. This plane intersects the second base line in a point where a line passing through the point will intersect both base lines.

Thus, with two non-intersecting base lines there will be one and only one line intersecting the two base lines passing through any point in space.

In the case of three non-intersecting base lines, any point of space can be associated with any two of the base lines (except special positions) and thus in each point of space there are three lines intersecting two of the base lines. More generally, for n number of lines, for each point of space there will be $n(n-1)/2$ lines intersecting two of the base lines and passing through the point.

Thus the invention involves analyzing a discontinuity from two or more non-intersecting base lines located outside the discontinuity slanted from each other and located in such a way that the discontinuity will be encompassed by lines joining all the points of any one base line to the points of all the other base lines.

Basically, a discontinuity is analyzed by monitoring the modification of a signal transmitted from various points of a base line and received on the various points of another base line after passing through the discontinuity.

The signal may consist of x-rays for short distances, electromagnetic signals for low conductive media, sonic or supersonic signals in other cases, or any other from of energy suited to the media.

Thus using a small number of boreholes it is possible to determine the location and the shape of a discontinuity with a coverage which would have, up to now, required a great number of boreholes.

In the same manner, in medicine, it is possible to obtain very good information on a discontinuity or anomaly in the human body without the need for considering a large number of planar sections.

Other advantages of the invention will become apparent from a consideration of the following detailed description and from the accompanying drawings.

BRIEF DESCRIPTION OF THE DRAWINGS

In the following drawings which are shown as non-limiting examples:

FIG. 1 is a schematic sectional view of the ground perpendicular to the surface showing non-intersecting boreholes located around a discontinuity to be analyzed;

FIG. 2 is a planar view of these boreholes and of the discontinuity;

FIG. 3 is a sketch on a larger scale showing two of the boreholes containing, respectively a transmitter and a receiver;

FIGS. 4 and 5 each show the representation by a surface of the distance traversed by a signal going through a discontinuity obtained by plotting said distance vertically in relation with the parameters of the signal lines and the base curve of these surfaces, according to one of the steps which may be employed in the implementation of the invention;

FIG. 8 is a schematic section of the ground perpendicular to the surface showing another aspect of the invention;

FIG. 10 shows a detection system which may be employed according to the invention;

FIG. 11 shows a possible position of three base lines in relation with the coordinate axis;

FIG. 12 is a schematic view of the upper part of a human leg and of the process as applied to imaging the upper bone of the leg.

DETAILED DESCRIPTION

Figure 6:
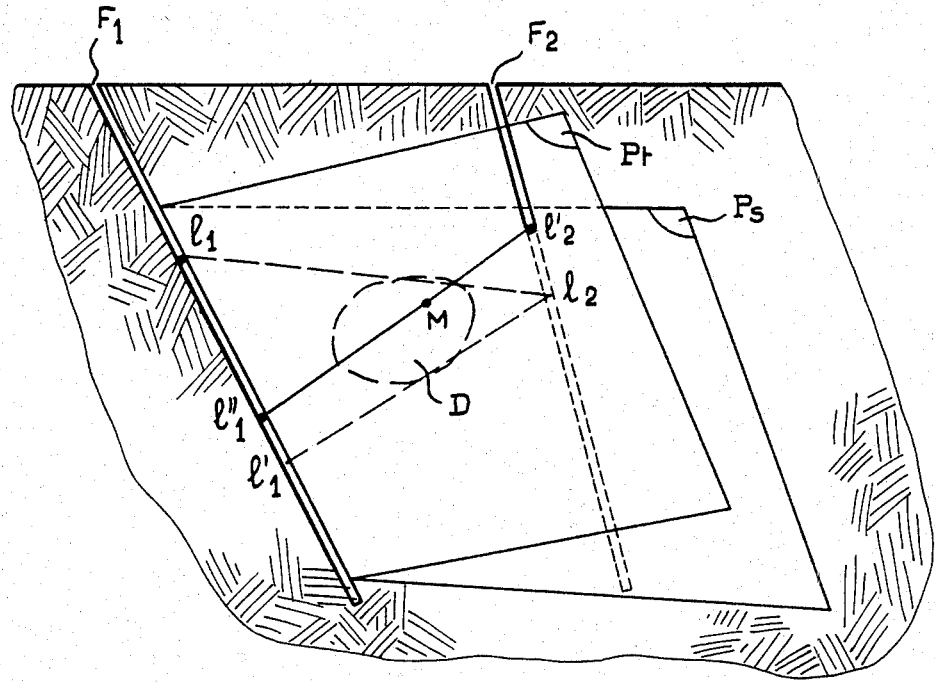
FIG. 6 is a sketch showing two boreholes and certain planes which are useful in describing one of the steps of the process.

The following paragraphs will show how the invention can be applied to the analysis of a discontinuity located underground.

FIGS. 1 and 2 show three straight boreholes $F_1$, $F_2$, $F_3$ drilled in the ground 1 slanted from the surface S, non-intersecting, and located around a discontinuity D. Modern control techniques for locating boreholes will give the exact position of the boreholes $F_1$, $F_2$ and $F_3$.

With reference to FIGS. 1 and 3, one of the boreholes, $F_1$ as an example, a transmitter 2 is lowered down (see FIG. 3) using a cable 3 and can be moved step by step by a motor 4. It is thus possible to obtain all along the borehole $F_1$ a number of transmission points by moving the transmitter 2, with the position of the transmitter being characterized by the distance $l_1$ between the transmitter and the head or mouth of the borehole $F_1$.

In borehole $F_2$, in the same manner, a receiver 5 held by cable 6 can be moved by a motor 7 through a number of reception points, characterized by the distance $l_2$ between the receiver 5 and the head of borehole $F_2$.

In the same way, in the borehole $F_3$ a receiver or transmitter is moved to a number of receiving or transmitting points characterized by their distance $l_3$ (see FIG. 1).

Transmitter 2 can be an ultrasonic transmitter and receiver 5 can register the variations of the ultrasonic signal coming from the transmitter 2 along the various signal paths or lines $l_1$, $l_2$ extending from the transmitter 2 to receiver 5.

In the same manner a transmitter-receiver system will monitor the various signals following signal lines or signal paths $l_1$ $l_3$ and $l_2$ $l_3$ which join the various points of transmission and reception of the boreholes $F_1$, $F_3$ and $F_2$, $F_3$.

By moving the various transmission and reception points in the boreholes $F_1$, $F_2$, $F_3$ one obtains all the signal lines such as $l_1$ $l_2$, $l_1$ $l_3$ and $l_2$ $l_3$ monitoring all of the volume between the boreholes $F_1$, $F_2$ and $F_3$ and, in particular, discontinuity D.

It is thus possible to obtain a table of the different signals received by the receivers for the signal lines $l_1$ $l_2$, $l_2$ $l_3$ and $l_1$ $l_3$ between the boreholes $F_1$, $F_2$ and $F_3$.

The distances $l_1$, $l_2$ $l_3$ being precisely known, the position of each of the signal lines is precisely known.

The alteration (such as the variation in attenuation or speed of travel, for example) of the signals received by the receiver 5 is a function of the distance traveled by the signal in the ground 1 and in the discontinuity D. As the discontinuity D has characteristics that are different from those of the ground 1 these alterations are a function of the distance the signal had to travel through the discontinuity.

It is thus possible to determine for each signal line or path $l_1$ $l_2$, $l_1$ $l_3$, $l_2$ $l_3$ the respective distances $d_{1-2}$, $d_{1-3}$, $d_{2-3}$ that the signal had to go through the discontinuity D.

Disconuity D can thus be characterized by three surfaces giving the distances $d_{1-2}$, for each signal line $l_1$ $l_2$, the distances $d_{1-3}$ for the signal lines $l_1$ $l_3$ and the distances $d_{2-3}$ for the signal lines $l_2$ $l_3$.

These surfaces are, in effect, similar to three pictures of the discontinuity as seen from three different angles; if the differential attenuation of the signal is used as the function to distinguish between travel in the earth and in the discontinuity, the darkness of the picture would be a function of the distance travelled through the discontinuity.

These surfaces can be represented in three axis orthogonal coordinates $d_{1-2}$, $l_1$, $l_2$ $d_{1-3}$, $l_1$, $l_3$, $d_{2-3}$, $l_2$, $l_3$. These surfaces (see FIGS. 4 and 5) have a base curve $C_{1-2}$, $C_{1-3}$, and $C_{2-3}$ respectively in the planes $l_1$, $l_2$; $l_1$, $l_3$; $l_2$, $l_3$; on these curves the distances $d_{1-2}$, $d_{1-3}$ and $d_{2-3}$ are zero.

All the signal lines characterized by parameters $l_1$, $l_2$ or $l_3$ situated outside these base curves do not intersect discontinuity D and therefore are of no interest.

The characteristic surfaces in d and l have their tangent plane perpendicular to the l plane along the base curve C.

FIG. 6 shows a plane $P_s$ containing a borehole $F_1$ and intersecting the discontinuity D. This plane $P_s$ intersects the borehole $F_2$ at a point characterized by a distance $l_2$ and the borehole $F_3$ (not shown on FIG. 6 for simplicity) at a point $l_3$. From each of these points $l_2$ and $l_3$ there are two signal lines such as $l_2$ $l_1$ and $l_2$ $ll'$ intersecting the borehole $F_1$ and tangent to the section of the discontinuity by the plane $F_1$ $l_2$ $l_3$.

These tangents are characterized on the borehole $F_1$ by the coordinate $l_1$ found on the base curves of the surfaces in $d_{1-2}$ and $d_{3-1}$ corresponding to the coordinates $l_2$ and $l_3$ where the plane $P_s$ intersects the boreholes $F_2$ and $F_3$.

In practice, if sonic or ultrasonic signals are used these tangents are characterized by a strong discontinuity in the reception of the signal due to the diffraction at the side of the discontinuity D.

For a plane $P_t$ tangent to the discontinuity D and containing borehole $F_1$, the two tangents to the section now reduce to a point, at discontinuity D, and passing by the intersection of plane $P_t$ with the boreholes $F_2$ and $F_3$ merge into one tangent and this tangent such as $l'_2$ and l″₁ passes through the point of tangency M of plane $P_t$ to the discontinuity D.

Figure 7:
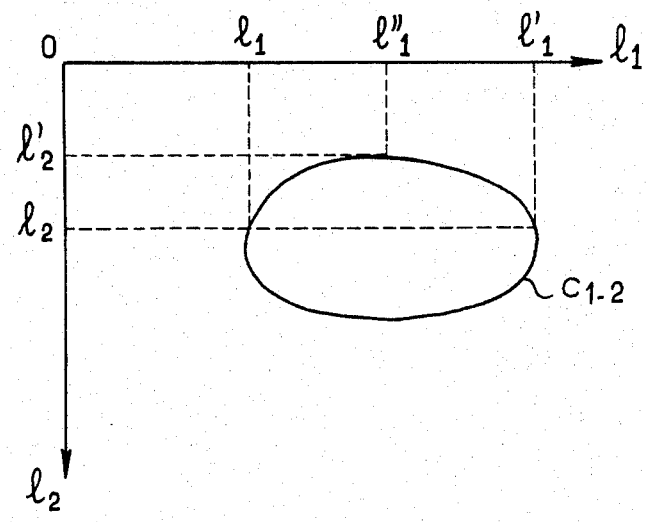
FIG. 7 shows a base curve utilized in one of the further steps of the process.

Such a tangent is characterized on the base curves of the characteristic surfaces $d_{1-2}$ and $d_{1-3}$ as shown by the curve $C_{1-2}$ on FIG. 7 by the points where the tangent of the base curve $C_{1-2}$ is parallel to the axis $l_1$.

Thus two tangents to discontinuity D can be found in plane $P_t$ and their intersection gives the point M where the plane $P_t$ is tangent to the discontinuity.

There are, at least six planes tangent to the discontinuity, two containing each one of the three boreholes $F_1$, $F_2$, $F_3$, and engaging opposite sides of the discontinuity, and the position of the six points of tangency are known by the intersection of two lines such as $l_2 l_1$, and $l_3 l_1$.

It has been shown that for each point of the volume located within the boreholes $F_1$ $F_2$ and $F_3$, there are three signal lines $l_1 l_2$; $l_1 l_3$ and $l_2 l_3$ clearly defined for which the distances $d_{1-2}$, $d_{1-3}$ and $d_{2-3}$ are also well defined.

Thus, at each point of tangency of the various planes $P_t$ determined by the intersection of two lines passes a third signal line intersecting the discontinuity D along a known distance d. Starting from the points of tangency and marking on the third signal lines the distances d, one can obtain six new points of the limit of the discontinuity D. By each of the six new points there are two new signal lines on which the respective distances d can be marked thus giving twelve new points defining the extent of the discontinuity.

It is therefore possible, by a step-by-step method, to establish the geometry of the discontinuity D while adjusting the positions to take into account the inevitable inacuracies when two points, issued from two different iterations are near each other, and thus obtain a consistent result.

It may be useful for special geometries of a discontinuity D (ie: very long cavity) to use more than three boreholes or to associate two or more boreholes to a surface line $L_3$ as shown on FIG. 8 where either the receiver or the transmitter are moved along line $L_3$ (see FIG. 8).

The method used, in such a case, for more that three boreholes is basically similar but whenever the more than three signal lines can be used, this will provide extra information. Furthermore, whenever the medium is heterogeneous, more signal lines will allow a better analysis.

On the other hand in the case of only two boreholes and when there is no surface base line there is only one signal line passing through any point of the volume to be analysed. It is then necessary, to accurately locate the discontinuity to obtain extra information such as that obtained by the backscatter or reflections from the discontinuity. This can also be useful when using more than two boreholes or baselines. For such purposes a receiver may be located with the transmitter, and distance determined in accordance with radar or sonar principles.

It is also possible to add an extra borehole in the same plane as one of the base boreholes to allow for a more thorough analysis of a section of the discontinuity; and this additional borehole can be replaced by a surface line.

Under certain conditions (in particular to analyze discontinuities of highly contrasting characteristics) it may be desirable because of refraction and diffraction effects, to repeat certain measurements by inverting the position of the receiver and the transmitter. In such a case, the signals may not generally follow a straight line, but the general approach is still valid.

In practice, whatever the number of boreholes and signal lines, the following steps are followed.

First, all the basic data must be gathered: characteristics of the medium outside the discontinuity and those, known or assumed, of the discontinuity.

Then in a first step the characteristic surfaces giving the distances $d_{1-2}$, $d_{1-3}$ etc. of the signal lines through the discontinuity D in function of the parameters $l_1 l_2$, $l_1 l_3$, $l_2 l_3$ intersecting the boreholes $F_1$ and $F_2$; $F_1 F_3$; $F_2 F_3$ are computed.

In the second step the geometry of the discontinuity D is established from these distances $d_{1-2}$, $d_{1-3}$, etc. In theory, the number of measurements to cover the total volume is infinite; however, in practice, one should use a series of closely spaced discrete measurements.

In order to rough out the problem it is possible to consider initially a limited number of points of transmission and reception evenly spaced on each borehole $F_1$ $F_2$ etc. chosen in relation to the overall size of the discontinuity D the type of signal which is used, etc. As an example for ultrasonic signals and a discontinuity D such as a cavity measuring a number of tens of meters a spacing of two to three meters between points can be considered. In such a case, either by moving transducers or by using an array of transducers spaced by two or three meters from each other in one of the boreholes, one would associate all of the points distant from each other by two or three meters in each borehole to all the other similar points in all the other boreholes.

All of the parameters $l_1 l_2$, etc. are stored in the computer memory and the approximate base curves corresponding to the zero distances $d_{1-2}$, $d_{1-3}$, for the various discrete signal lines or paths, are then determined. These approximate curves will show the regions outside the discontinuity D on one hand and, on the other, the critical zones where the number of measurements should be increased, and they also give the characteristics of the tangent planes $P_t$.

The exact position of the signal paths or lines $l_1 l_2$, $l_1 l_3$, etc. joining two boreholes being known, the computer can determine the coordinates of the point of tangency of the planes $P_t$. The next step is to determine, relative to the third signal line passing through the tangent point, the length through the discontinuity given by the surfaces in $d_{1-2}$, $d_{1-3}$, etc. by extrapolation, between two measured signal lines or paths, if necessary. The computer will now calculate the coordinates of the third signal line and mark the distance through the discontinuity from the point of tangency.

From these new points whose positions are stored in the computer memory the computer computes the two new signal paths or lines passing through these points and marks on these lines the distances through the discontinuity given by the surfaces $d_{1-2}$ etc. and will store these new points in the computer memory. Thus by an iterative process the exact geometry of discontinuity D is established, the computer storing in memory the position of the surface points only. Quite frequently two of the computed points may be quite close. In such a case only a medium position is considered and stored in memory.

All the results will then be balanced by continuity so as to obtain a convergent solution.

It may appear that coherance of the results may be difficult to obtain when a heterogeneous medium is encountered. It may then be useful to add a fourth borehole so as to add redundancy in the analysis which allow the use of reconstitution algorithm by the finite element method.

Figure 9:
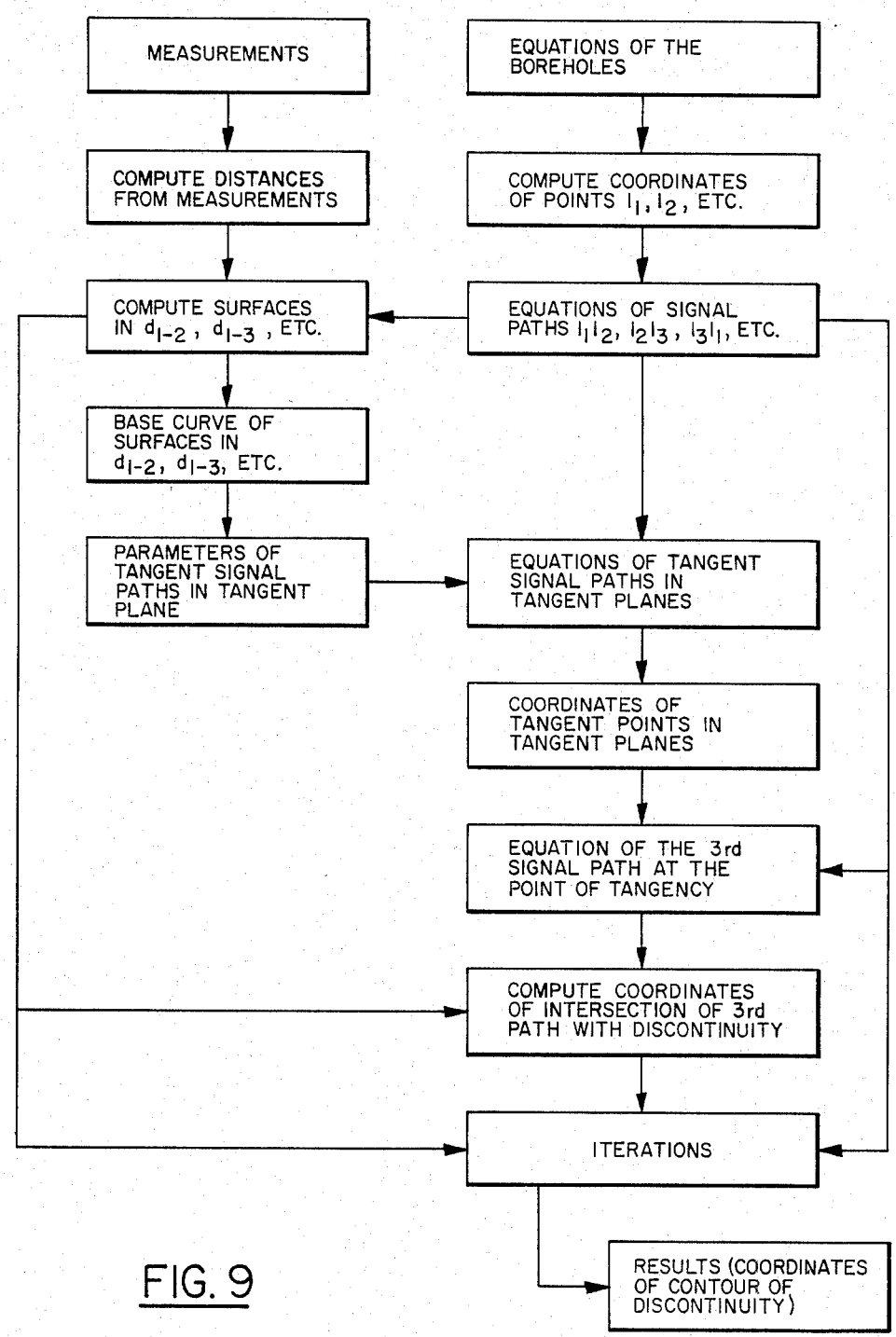
FIG. 9 is a block diagram of various steps which may be employed in the process.

The computer process is shown schematically in FIG. 9.

We have thus shown that the process, as described, allows, by using a limited number of boreholes or base lines, straight or curved, and carrying transducers, the determination of the location and shape of one or more discontinuities located between these boreholes or base line.

FIG. 10 is a block diagram of an illustrative system for implementing the present invention. This system includes non-intersecting boreholes $F_1$, $F_2$ carrying respectively a transmitter 2 and a receiver 5 connected to positioning means 30, 31, so that the exact positions of the transmitter and the receiver in the boreholes is monitored at all times. The transmitter 2 is connected to a signal generator 32. The receiver 5 is connected to a filter 33 and an amplifier 34. The signal generator and the amplifier 34 are linked to a unit 35 that measures the transit time of the signals.

A computer 36 stores in its memory the distances measured through units 30 and 31 and the transit times given by unit 35. This computer is linked to a printing unit 37 and to a video monitor screen 38 to given an image of the discontinuity.

A numerical example is now given to illustrate the process of the invention.

We shall consider, to simplify, three base lines $F_1$, $F_2$, $F_3$ perpendicular to each other (see FIG. 11), and $O_z$.

Any other set up can be deduced from this one by a homothetic transformation.

The equations of the three base lines will be:

$$F_1: x, y = o, z = a$$

$$F_2: x = b, y, z = 0 \quad (1)$$

$$F_3: x = 0, y = c, z = 0 \quad (1)$$

For a point in space of coordinates X, Y, Z, the equations of the planes containing this point and one of the base lines shall be:

$$F_1 \frac{Z-a}{aY} y - \frac{1}{a} z + 1 = 0 \quad (2)$$

$$F_2 \frac{X-b}{bZ} z - \frac{1}{b} x + 1 = 0$$

$$F_3 \frac{Y-c}{cX} x - \frac{1}{c} y + 1 = 0$$

The parameters on the base lines of a signal line joining two base lines will be as previously used:

$l_{12}$ and $l_{21}$; with $l_{12}$ on $F_1$ and $l_{21}$ on $F_2$
$l_{23}$ and $l_{32}$; with $l_{23}$ on $F_2$ and $l_{32}$ on $F_3$
$l_{13}$ and $l_{31}$, with $l_{13}$ on $F_3$ and $l_{31}$ on $F_1$
From (1) and (2) we get:

$$l_{12} = \frac{X-b}{Z} a + b \quad l_{21} = \frac{aY}{a-Z} \quad (3)$$

$$l_{23} = \frac{Y-c}{X} b + c \quad l_{32} = \frac{bZ}{b-X}$$

-continued $$l_{31} = \frac{Z-a}{Y} c + a \quad l_{13} = \frac{cX}{c-Y}$$

The equations of the signal lines or paths will be:

$$F_1F_2 \frac{x-l_{12}}{b-l_{12}} = \frac{y}{l_{21}} = \frac{a-z}{a} \quad (4)$$

$$F_2F_3 \frac{y-l_{23}}{c-l_{23}} = \frac{z}{l_{32}} = \frac{b-x}{b}$$

$$F_3F_1 \frac{z-l_{31}}{a-l_{31}} = \frac{x}{l_{13}} = \frac{c-x}{b}$$

When three signal lines intersect at a point, from (3) we have the following equations.

$$l_{31} = a\left(1 - \frac{c}{l_{21}}\right) \quad (5)$$

$$l_{12} = b\left(1 - \frac{a}{l_{32}}\right)$$

$$l_{23} = c\left(1 - \frac{b}{l_{13}}\right)$$

These three equations can be used to check the coherence and adjust the experimental results. Three signal lines intersect in a point with the following coordinates X, Y, Z derived from (3):

$$X = b \frac{acl_{13} - al_{13}l_{21} + l_{13}l_{21}l_{32}}{abc + l_{13}l_{21}l_{32}} \quad (6)$$

$$Y = c \frac{abl_{21} - bl_{21}l_{32} + l_{21}l_{32}l_{13}}{abc + l_{13}l_{21}l_{32}}$$

$$Z = a \frac{bcl_{32} - cl_{32}l_{13} + l_{21}l_{32}l_{13}}{abc + l_{13}l_{21}l_{32}}$$

Further, the distance between two base lines along a signal line is equal to:

$$\overline{l_{12}l_{21}} = \sqrt{(l_{12} - b)^2 + (l_{21})^2 + a^2} \quad (7)$$

$$\overline{l_{23}l_{32}} = \sqrt{(l_{23} - c)^2 + (l_{32})^2 + b^2}$$

$$\overline{l_{31}l_{13}} = \sqrt{(l_{31} - a)^2 + (l_{13})^2 + c^2}$$

For a sonic signal moving from one base line to the other with a sound speed equal to $v_1$, the transit time shall be:

$$t_{12} = \frac{\overline{l_{12}l_{21}}}{v_1} \quad t_{23} = \frac{\overline{l_{23}l_{32}}}{v_1} \quad t_{31} = \frac{\overline{l_{31}l_{13}}}{v_1} \quad (8)$$

The problem can then be solved using these basic equations.

Now consider a simple case where the three base lines are on the side of a cube and where the discontinuity is a sphere in which the speed of the sound is $v_2$, this sphere situated in a medium with a speed of the sound of $V_1$. We also assume that the center of the sphere is at the center of the cube. If the signal lines must intercept the whole of the sphere, and if a plane tangent to the sphere and containing a base line must intersect the two other base lines, the diameter d of the sphere must be smaller than the side of the cube.

So $a = b = c > d$

And, in order to have the signal lines reasonable short, the base lines should be such that: $a = b = c \geq 3d$ So let us take $a = b = c = 3d$ The parameters of the points where a plane containing $F_1$ and tangent to the sphere intersects $F_2$ and $F_3$ will be found to be $l_{31} = 0.39a$, and $l_{21} = 1.64a$, and the corresponding parameters of the tangent lines on $F_1$ will be $l_{12} = 0.22a$ and $l_{13} = 1.21a$ for a sphere centered in $x = y = z = a/2$.

The signal lines of parameter $l_{12} = 0$ $l_{21} = a$, $l_{23} = 0$ $l_{32} = a$ and $l_{31} = 0$ $l_{13} = a$, intersect at the center of the sphere with the maximum distance through the sphere of $a/3$.

Suppose now that one wishes to determine the shape and the position of a cavity similar to the above sphere.

The speed of sound inside the cavity is $v_2$ and outside $v_1$ with $v_1 > v_2$.

The time of transit for sound outside the cavity is:

$$\frac{\overline{l_{12}l_{21}}}{v_1} = \frac{\sqrt{(l_{12} - a)^2 + (l_{21})^2 + a^2}}{v_1} \text{ etc} \ldots \quad \text{(9-A)}$$

If a signal path passes through the cavity over a distance d the total transit time on the signal line will be:

$$\frac{\overline{l_1l_2} - d}{v_1} + \frac{d}{v_2} = \frac{\overline{l_1l_2}}{v_1} + d\left(\frac{1}{v_2} - \frac{1}{v_1}\right) \quad \text{(9-B)}$$

and $$dt = d\left(\frac{1}{v_2} - \frac{1}{v_1}\right) \quad \text{(9-C)}$$

$$d = \frac{v_1 v_2}{v_1 - v_2} dt$$

Knowing $v_1$ and $v_2$, d is then found from Equation (9-C).

In the above example, by sweeping through the cavity and using function (9-C) with the various paths $l_1l_2$, $l_2l_3$, and $l_3l_1$, the computer will establish the characteristic surface giving the distances d for the various $l_1l_2$, etc. and the corresponding base curves.

In this case, it will be found that characteristic surface will have a maximum of a $a/6$ for $l_1 = 0$, $l_2 = a$ and the base curve has a tangent parallel to the $l_1$ axis for $l_1 = 1.64a$ and $l_2 = 0.22a$.

Similarly, the base curve for the $l_1l_3$ will have a tangent to the $l_1$ axis for $l_1 = 1.21a$ and $l_3 = 0.39a$.

These two signal lines intersect at a point whose coordinates are given by equation (3).

To check that the signal lines properly intersect, one will use equation (5).

If equation (5) shows that the lines do not intersect properly, the signal paths will have to be adjusted. In our present example, it will be found that the signal paths intersect in the point:

$x = 0.5a$; $y = 0.587a$; $z = 0.642a$

From this position and using equation (3) the coordinates $l_{23}$ and $l_{32}$ are computed for the third signal line. The characteristic surfaces in d for $l_2l_3$ will give the distance of this signal line through the cavity and, step by step, the whole geometry is determined.

The invention can also be applied to the analysis and imaging of discontinuities and anomalies or internal injuries of the bodies of humans or animals. Such an application is shown in FIG. 12 showing a leg 10 in which an anomaly has to be investigated in the joint 12 of the femur 11 in the pelvis 13. In such a case two water cushions 14 and 15 filled with liquid 16 are placed on each side of leg 10 so that the shape of the cushions 14 and 15 conform to the profile of the leg 10. Inside these cushions 14 and 15 are the base lines 17 and 18 that do not intersect and that carry either ultrasonic or other transmitters 19 and corresponding receivers 20 evenly spaced apart.

According to this embodiment of the invention the transmitters 19 are triggered in sequence so as to obtain all the signal paths joining the transmitters 19 to the receivers 20. The shape and dimensions of the anomaly are then determined as shown previously.

It is thus possible for two or more transducer base lines to obtain accurate information on an anomaly without having to use a number of parallel planar sections, and to image the volume in three dimensions.

As shown in the above example, the distance through the discontinuity is first calculated on each line for all the signal lines. The computer stores in memory this distance for each line. All the lines of the same plane are selected together and, if necessary, these distances can be mathematically smoothed for reasons of continuity.

The computer determines the points of tangency and the coordinates of such points (normally six for three boreholes) and indicates that these lines of tangency have been used. At this stage, the surface of the discontinuity is only known by these points of tangency and by the corresponding tangent lines. These points and the tangent lines are then stored, i.e. in rectangular coordinates.

One must then find, in a given point, the signal lines passing through this point and that have not yet been used to define the discontinuity. These lines are easy to find in each of the planes that include the point and each of the boreholes. If need be, an intermediate plane obtained through an interpolation, can be used.

Then the distance through the discontinuity from the given point is used. If no analyzed signal line passed exactly through the point, then the distance is obtained from two adjacent signal lines in the same plane. The computer then stores this line in memory.

From the given point and the distance, a new point on the surface of the discontinuity is obtained and stored in the computer memory. If there is any doubt as to the position of this new point or if the corresponding tangent is not known, continuity is used to obtain a good estimated location. The tangent in the starting point is used to determine, in the planar section, the tangent in the final point (coordinating the result with those of the adjacent lines).

If the new point is close to an already determined point, it has to be coherent with the tangents; if this is not the case, the extreme points will be ignored. The procedure is then carried on so as to find other points of the discontinuity corresponding to known signal lines, and this is continued until a sufficient number of valid points to fully characterize the discontinuity are obtained. If there are not enough points, a criterion of continuity will be employed for intermediate points.

From all these determined points, it is then easy to image the discontinuity in any form required, using available video display systems. It is, for example, practical to image the discontinuity through a number of planar sections through selected planes. It is also practical to display an isometric or perspective view of the discontinuity. In the same manner, the discontinuity can be shown in shadows more or less deep, corresponding to the depth or thickness of the discontinuity.

Figure 13:
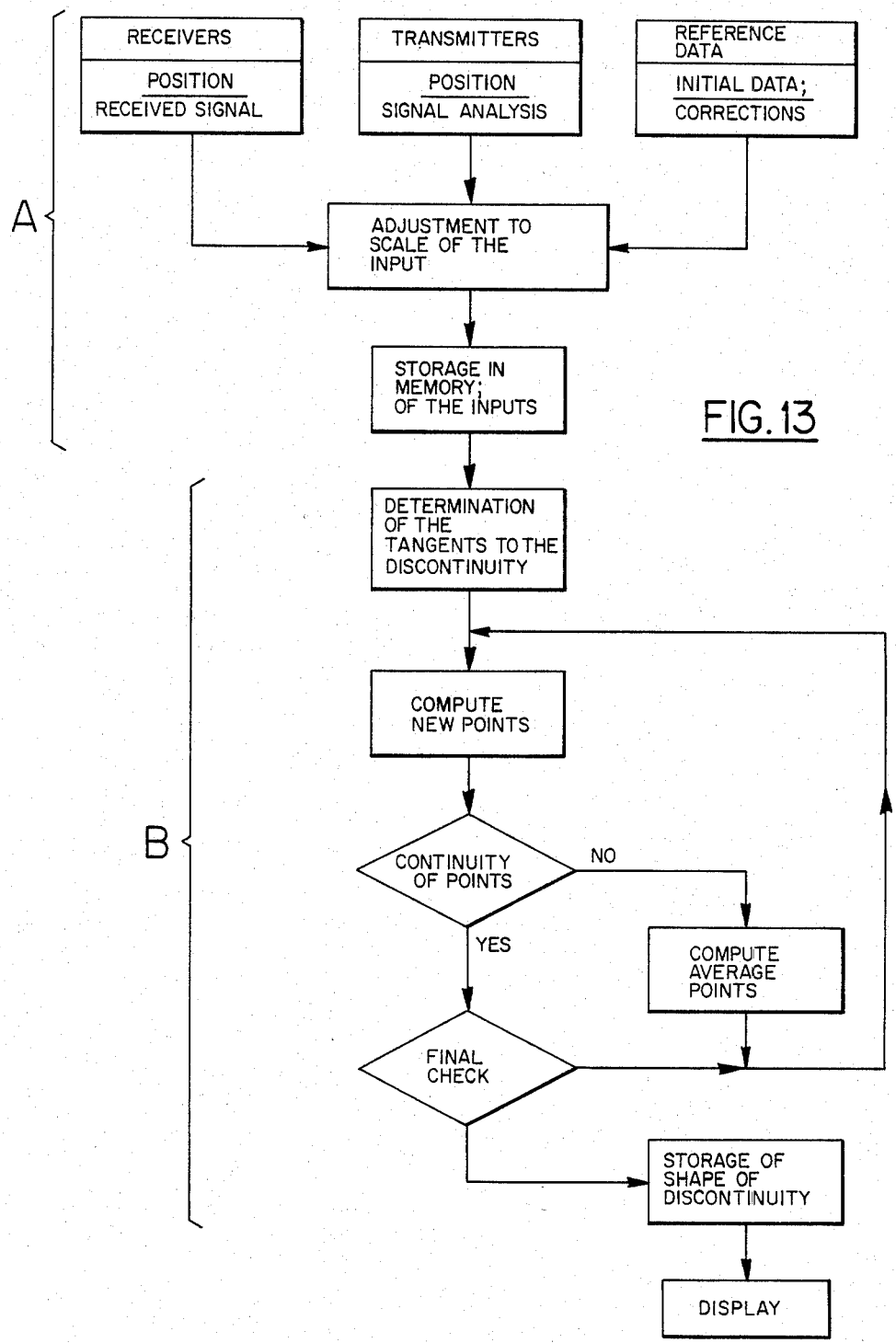
FIG. 13 is another diagram showing various steps which may be employed in the implementation of the invention.

These various stages are shown on the diagram of FIG. 13, where one portion A of the system involves the introduction of the data into the computer and B the reconstruction of the discontinuity from this data.

Naturally, the invention is not limited to the above examples and many modifications can be introduced without going outside the scope of the invention. As other examples, the discontinuity to be analyzed may involve objects immersed in a liquid, or temperature discontinuities either underground or inside the human body. For the determination of an underground discontinuity, one of the boreholes can be perpendicular to the surface of the ground, but it is desirable that at least two boreholes or transducer lines do not intersect and that the lines joining those two boreholes or base lines intercept the whole of the volume to be analysed. The transducer lines need not be straight and can be replaced by either parts of a circle or by other curves, preferably curves which are readily susceptible of mathematical analysis as to location of the system components and the like. The whole of the measurement and analysis can be done automatically by using a predetermined steps and the computed results can either be printed or displayed on a screen or presented in any desired manner. Alternatives involve the use of collimated signals, or signals modulated in frequency or in phase, or a series of pulses in order to get a better identification. As noted above, echos and diffracted signals may also be detected. Further, in a heterogeneous medium, additional boreholes (or base lines) either intersecting one of the boreholes, or non-intersecting, may be employed, to provide redundancy or further date for averaging to improve the resolution of the image or configuration data. Accordingly, the present invention is not limited to the system and method as shown in the drawings and described in detail hereinabove.

What is claimed is:

1. A method for imaging discontinuities in an otherwise reasonably homogeneous medium, comprising the steps of:
   providing at least two non-intersecting and non-parallel base lines, on opposite sides of the discontinuity to be imaged;
   transmitting signals which will pass through the medium toward said discontinuity from a succession of transmission points along a first one of said base lines;
   picking up signals at a succession of points along a second one of said base lines from each of a plurality of said transmission points;
   measuring transmission characteristics for said signals between each transmission point and each pick-up point;
   determining characteristics of signal transmission through said homogeneous medium outside of said discontinuity;
   determining the difference between the measured signal and the calculated signal for the distance in a homogeneous medium between each pair of transmission and pick-up points;
   determining whether each said point-to-point transmission occurred entirely outside of or partly through said discontinuity;
   determining the distance of travel within the discontinuity for each said point-to-point transmission; and
   calculating the configuration and location of said discontinuity from said measurement.

2. A method as defined in claim 1 including the additional step of determining the location of a series of planes tangent to the discontinuity.

3. A method as defined in claim 1 characterized by the use of three base lines located around the discontinuity.

4. A method as defined in claim 3 including the step of determining the coordinates of the points of tangency between said tangent planes and said discontinuity.

5. A method as defined in claim 1 characterized by the fact that the base lines are substantially straight.

6. A method as defined in claim 1 characterized by the fact that the base lines are boreholes and including the steps of moving a transmitter along the length of one of said boreholes, and moving a receiver along the length of another of said boreholes.

7. A process as defined in claim 1 characterized by the fact that the successive points of transmission and reception are obtained by moving the transmitter and receiver step by step along the said base lines.

8. A process as defined in claim 1 characterized by the fact that a succession of equally spaced transducers are located along one of the base lines and are triggered in succession according to a predetermined sequence.

9. A method as defined in claim 1 including the step of initially establishing or defining the position of the base lines relative to one another.

10. A method as defined in claim 1 including the intermediate step of calculating the distances through the discontinuity and determining the configuration of a three-dimensional surface representing said thicknesses.

11. A process as defined in claim 1 including the step of holding liquid in flexible containers against a body, and transmitting signals and receiving them through said containers.

12. A process as defined in claim 1 applied to the analysis of discontinuities in a human or animal body, characterized by the fact that a number of transmission points and receiving points are moved on at least two base lines that do not intersect located outside the body on each side thereof.

13. A system as defined in claim 1 including flexible walled liquid containers and means for mounting said transmitting and said receiving means to send and receive signals through said containers.

14. A system for imaging discontinuities in an otherwise reasonably homogeneous medium, comprising:
   means providing at least two non-intersecting and non-parallel base lines on opposite sides of the discontinuity to be imaged;
   means for transmitting signals which will pass through the medium toward said discontinuity from a succession of transmission points along a first one of said base lines;
   means for picking up signals at a succession of points along a second one of said base lines from each of a plurality of said transmission points;

means for measuring transmission characteristics for said signals between each transmission point and each pick-up point;

means for determining characteristics of signal transmission through said homogeneous medium outside of said discontinuity;

means for determining the difference between the measured signal and the calculated signal for the distance in a homogeneous medium between each pair of transmission and pick-up points;

means for determining whether each said point-to-point transmission occurred entirely outside of or partly through said discontinuity;

means for determining the distance of travel within the discontinuity for each said point-to-point transmission; and means for calculating the configuration and location of said discontinuity from said measurements.

15. In a system for determining the location of discontinuities in a reasonably homogeneous medium:

transmitting means for generating signals which will traverse said homogeneous medium;

receiving means for receiving signals from said transmitting means after passing through said medium;

means for actuating said transmitting means to send signals toward said discontinuity from a succession of points along a first line;

means for actuating said receiving means to receive signals from said transmitting means at a plurality of points along a second line for each transmission point; said second line being non-intersecting and non-parallel with respect to said first line, and being located on the other side of said discontinuity with respect to said first line;

means for determining differences in each point-to-point signal transmission through said discontinuity as compared with signals transmitted over the same distance wholly in the homogeneous medium, and subsequently determining the distance of travel in the discontinuity for each point-to-point signal transmission; and means for calculating and displaying the configuration of said discontinuity from said determined individual point-to-point distances travelled within said discontinuity.

16. A system as defined in claim 15 including at least two boreholes extending respectively along said first and second lines.

17. A system as defined in claim 16 including means for moving said transmitting and receiving means up and down slanted boreholes.

* * * * *